US007816133B2

(12) United States Patent
Gibbs et al.

(10) Patent No.: US 7,816,133 B2
(45) Date of Patent: Oct. 19, 2010

(54) PREPARATION OF FIBROBLAST-POPULATED CONNECTIVE TISSUE SUBSTITUTE

(75) Inventors: Susan Gibbs, Amsterdam (NL); Edith Margaretha de Boer, Amsterdam (NL); Gudula Kirtschig, Amstelveen (NL); Riekeld Johannes Scheper, Amsterdam (NL); Derk Pieter Bruynzeel, Abcoude (NL)

(73) Assignee: Vereniging Voor Christelijk Hoger Onderwijs Wetenschappelijk Onderzoek En Patentienzorg, Amsterdam (NL)

( * ) Notice: Subject to any disclaimer, the term of this patent is extended or adjusted under 35 U.S.C. 154(b) by 1066 days.

(21) Appl. No.: 10/585,299

(22) PCT Filed: Jan. 14, 2005

(86) PCT No.: PCT/NL2005/000026
§ 371 (c)(1),
(2), (4) Date: Jul. 6, 2006

(87) PCT Pub. No.: WO2005/068614
PCT Pub. Date: Jul. 28, 2005

(65) Prior Publication Data
US 2009/0016994 A1    Jan. 15, 2009

(30) Foreign Application Priority Data
Jan. 16, 2004    (WO) ............... PCT/NL2004/000039

(51) Int. Cl.
C12N 5/071    (2010.01)
C12N 5/04    (2006.01)
(52) U.S. Cl. .................. 435/371; 435/373; 435/382; 435/393
(58) Field of Classification Search ................ 435/371, 435/373, 382, 393, 93.7
See application file for complete search history.

(56) References Cited

U.S. PATENT DOCUMENTS 6,846,675 B2 *    1/2005    Conrad et al. ............... 435/371

OTHER PUBLICATIONS

Basset-Seguin N et al: "Reconstituted skin in culture: A simple method with optimal differentiation" Differentiation, vol. 44, No. 3, Sep. 1990, pp. 232-238, XP000571262 ISSN: 0301-4681 the whole document.
Lee Dong-Youn et al: "A new skin equivalent model: Dermal substrate that combines de-epidermized dermis with fibroblast-populated collagen matrix" Journal of Dermatological Science, vol. 23, No. 2, Jun. 2000, pp. 132-137, XP002301200 ISSN: 0923-1811 cited in the application the whole document.
Chakrabarty K H et al: "Development of autologous human dermal-epidermal composites based on sterilized human allodermis for clinical use" British Journal of Dermatology, vol. 141, No. 5, Nov. 1999, pp. 811-823, XP002301201 ISSN: 0007-0963 the whole document.
Ghosh M M et al: "A comparison of methodologies for the preparation of human epidermal-dermal composites." Annals of Plastic Surgery, vol. 39, No. 4, Oct. 1997, pp. 390-404, XP000878553 ISSN: 0148-7043 cited in the application the whole document.
Ralston D R et al: "The requirement for basement membrane antigens in the production of human epidermal/dermal composites in vitro" British Journal of Dermatology, vol. 140, No. 4, Apr. 1999, pp. 605-615, XP002301202 ISSN: 0007-0963 the whole document.
Krejci N C et al: "In-vitro reconstitution of skin: Fibroblasts facilitate keratinocyte growth and differentiation on acellular reticular dermis" Journal of Investigative Dermatology, vol. 97, No. 5, Nov. 1991, pp. 843-848, XP008037008 ISSN: 0022-202X the whole document.

* cited by examiner

Primary Examiner—Ruth A Davis
(74) Attorney, Agent, or Firm—Paul, Hastings, Janofsky & Walker LLP

(57) ABSTRACT

Disclosed is a method for in vitro growing of connective tissue substitute, said connective tissue substitute being populated with fibroblasts, a connective tissue substitute obtainable by such a method, as well as a method for closing of a wound, wherein such connective tissue substitute is applied onto a wound.

18 Claims, 1 Drawing Sheet

PREPARATION OF FIBROBLAST-POPULATED CONNECTIVE TISSUE SUBSTITUTE

Figure 1:
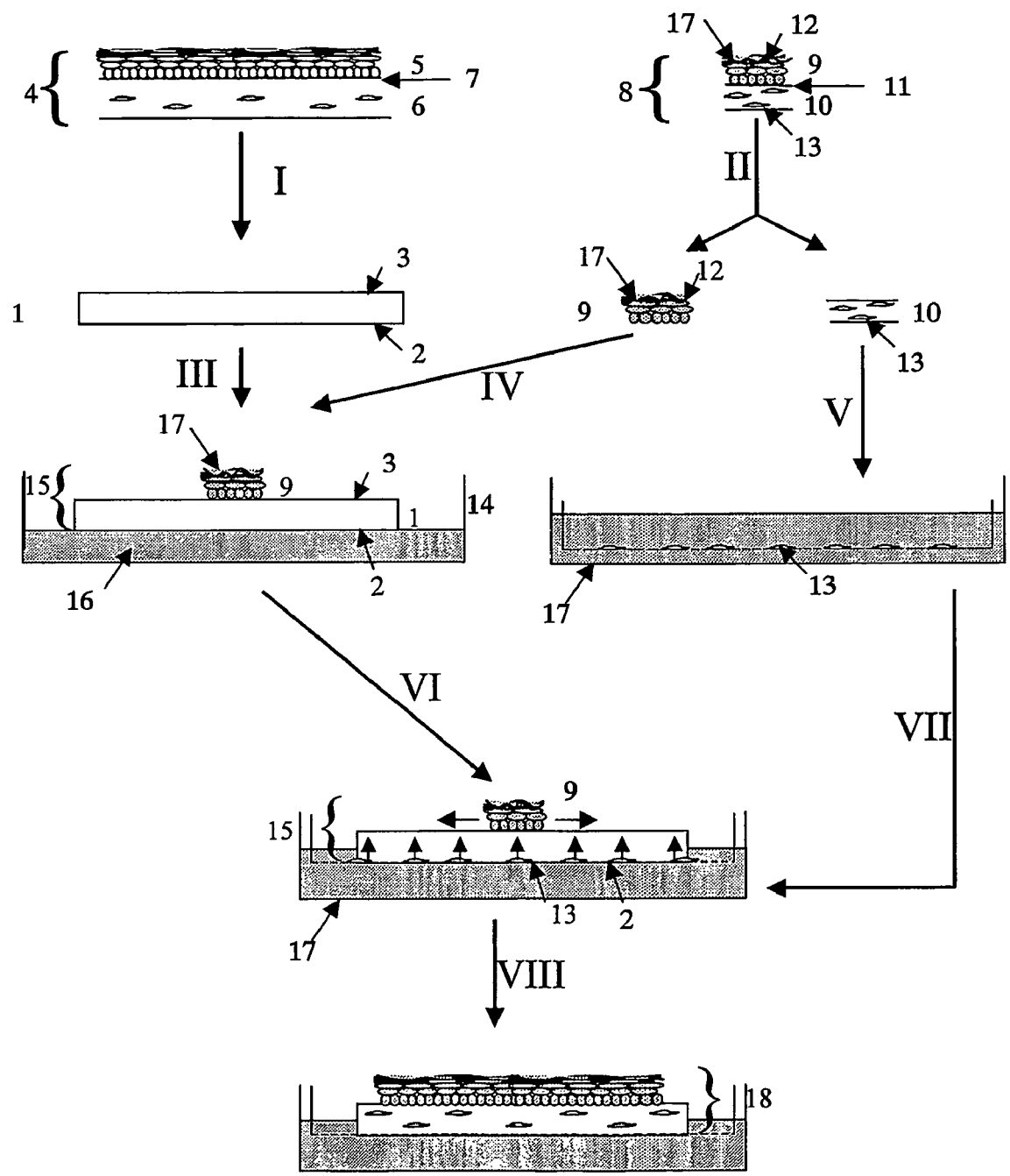

This application is the National Stage of International Application no. PCT/NL2005/000026 filed Jan. 14, 2005, which claims the benefit of International Application no. PCT/NL2004/00039 filed Jan. 16, 2004, the contents of which are incorporated by reference herein.

The present invention relates to a method for in vitro growing of connective tissue substitute of a subject, said connective tissue substitute being populated with fibroblasts, a connective tissue substitute obtainable by this method, as well as a method for closing of a wound applying said connective tissue substitute. Moreover, the present invention relates to a method for treating a subject suffering from a wound, comprising applying said connective tissue substitute onto the wound.

Artificial skin tissue substitutes are important for treatment of wounds, e.g. burn wounds, chronic wounds, plastic and/or surgery wounds and scars. Many such substitutes are in development or have recently been introduced onto the market.

Skin tissue comprises two cellular layers, namely an outer epidermal layer (epithelial tissue; also referred to as epidermis) and an inner dermal layer (connective tissue; also called dermis). The dermal layer is in contact with the epidermal layer through a basement membrane. The epidermal layer provides a barrier against infection and moisture loss, whereas the dermal layer is responsible for the elasticity and mechanical integrity of the skin. The dermal layer comprises the blood vessels that are responsible for the nutrition of the epidermal layer, and cutaneous sensory nerves traverse the dermal tissue into the epidermal tissue. Moreover, additional skin components, such as e.g. hair follicles and/or sweat glands, breach the epidermal and dermal layers. The basement membrane is a large extracellular protein matrix and plays an important role in the maintenance of skin tissue architecture and in anchoring basal keratinocytes present in the epidermis. Fibroblasts are a major component of the dermis and play an important role in the synthesis and reorganisation of extracellular matrix that occur during wound repair.

Regeneration of the epithelium, e.g. epidermis, which is important for wound closure and for protection against infection, relies on residues of epithelial cells that lie deep within the connective tissue structures, in the case of epidermal cells e.g. reté ridges and hair follicles. Closure of a wound by ingrowth of the epithelial layer from the edges of a wound will be insufficient for wounds larger than a few cm across.

Thus, in such cases wound closure requires a material to restore the epithelial barrier function and actually become incorporated into the healing wound. In contrast therewith, some materials may merely cover the wound to create an improved environment for epithelial regeneration by providing a temporary barrier against infection and controlling moisture losses.

Several skin tissue substitutes formed from allogeneic cultured cells are commercially available in combination with biomaterials as treatments to provide wound cover and stimulate wound closure (e.g. Apligraf® (Organogenesis Inc., Canton, Mass., USA, and Novartis Pharmaceuticals Corporation, East Hanover, N.J., USA), Transcyte® (Advanced Tissue Sciences Inc., LaJolla, Calif., USA), and Dermagraft® (Advanced Tissue Sciences Inc., LaJolla, Calif., USA)). Herein, the term "allogeneic" refers to tissue or cells derived from one or more different individual subjects of the same species.

For example, Apligraf® is composed of a gel of bovine collagen and living neonatal allogeneic fibroblasts with an overlying cornified epidermal layer of neonatal allogeneic keratinocytes, Transcyte® is composed of nylon mesh fabric which is seeded with neonatal fibroblasts, and Dermagraft® is manufactured by cultivating neonatal allogeneic fibroblasts on a polymer scaffold (the neonatal cells are all derived from a pool of foreskin obtained by circumcision of a pool of male babies). Cadaveric allograft (from non-profit skin banks) consists of intact dead skin and provides a temporary cover but will not provide direct wound closure.

In contrast to the above products that merely provide wound cover and speed up the healing process of the wound, also skin substitutes that provide wound closure are commercially available, such as Alloderm® (LifeCell, Woodlands, Tex., USA), Integra® (Integra Life Science Corporation, Plainsboro, N.J., USA).

Alloderm® is processed human cadaveric skin from which the epidermal layer has been removed and the cellular components of the dermal layer have been extracted in order to avoid a specific immune response. After application onto a wound, it is repopulated by host cells, revascularised and incorporated into the tissue. It therefore functions as a template for dermal regeneration and does not provide a cover as to provide a barrier against infection or for control of moisture losses.

Integra® has a bilaminar structure consisting of cross-linked bovine collagen and glycosaminoglycan, coated on one side with a silicone membrane that provides epidermal function. After application onto a wound, the collagen layer is biointegrated with the wound to form a vascular neodermal layer. This process takes about 3-6 weeks. Following this process, the silicone membrane can be removed and an ultra-thin split-skin graft applied. As such, closure of a wound using Integra® is a two-stage process.

Grafts consisting only of a dermal component, such as e.g. Alloderm®, are open to infection and water loss. Furthermore epidermis has to be generated from the wound edges and fibroblasts have to migrate into the dermis. In contrast therewith, grafts consisting of only an epidermal component such as e.g.: Epibase® (Genévrier Biotechnologie, Sophia-Antipolis Cedex, France) are generally very fragile. The basement membrane has to be formed with the dermis present in the wound bed, which is a process that takes a number of weeks. Furthermore, such a graft is not very differentiated. Therefore, the barrier of such a graft will be inferior to skin or a full skin graft.

Moreover, Alloderm® has the drawback that it does not provide an autologous cover; Integra® comprises a non-human matrix and involves a time-consuming two-stage process and cadaveric allograft may provoke a host immune response and thus graft rejection.

Autologous grafts or skin tissue substitutes that provide immediate wound closure rather than just wound cover that are easily and quickly formed and do not comprise allogeneic materials are not yet commercially available. It is important that such materials provide wound closure and are not rejected by the host. Moreover, it is important that such materials do not comprise allogeneic cells such as human foreskin cells to prevent a risk of rejection, inflammation due to rejection and also cross-infection. In addition, such skin substitutes preferably do not comprise a non-human matrix, such as a bovine collagen matrix, to avoid issues associated with such non-human matrix.

Dong-Youn Lee et al. (J. Dermatol. Sci. (2000) 23:132-137) reports a dermal substrate that combines de-epidermised dermis (DED) with a fibroblast-populated collagen matrix. From human foreskin, keratinocytes and fibroblasts were isolated and cultured. Second-passage cells were used for the preparation of the dermal substrate. In order to obtain the fibroblast-populated collagen matrix, fibroblasts have to be used in amounts of $3\times10^5$ cells/ml. Such amounts of cells are not suitable for the commercial preparation of autologous dermal substitutes, as obtaining such amount of cells will require either large biopsies or extensive passaging of fibroblasts. Thus, this method is only applicable on allogeneic material (in casu allogeneic foreskin tissue), or only when preparation is allowed to take a relatively long time.

Ghosh et al. (Ann. Plastic Surgery (1997) 39: 390-403) discloses a dermal tissue substitute prepared by the following method. DED was placed with its reticular surface up in a well of a tissue culture dish, a ring was placed on top of the reticular surface and pressed firmly down on the surface as to ensure a tight fit between the dermis and the ring. Fibroblasts and keratinocytes were isolated from split-thickness skin grafts and were serially passaged, and then cell suspensions were prepared. The fibroblasts were added to the ring, and cultured during 24 hours. Next, the ring was removed and the fibroblasts were cultured for an additional 7 days. Then, the DED was turned over as to expose its papillary surface to the air. Again a ring was pressed into the surface, and the ring was now filled with keratinocytes. These were cultured during 24 hours, then the ring was removed, and the keratinocytes were cultured for an additional 7 days. It was shown that the fibroblasts populated the DED, and the epidermal layer was fully differentiated. This method has the distinct disadvantage that fibroblasts and keratinocytes have to be serially passaged in order to obtain amounts of cells sufficient for the preparation of the dermal tissue substitute. Every passage takes about a week, such that this step required a relatively large amount of time. Moreover, the DED has to be turned over during substitute preparation in order to obtain the fibroblast populated DED, which is inconvenient.

As such, it is a first object of the present invention to provide a simple and fast method for the in vitro preparation of connective tissue layer, preferably an autologous dermal layer, to provide for wound closure, in particular for facilitated repopulation of the wound bed. Preferably, this connective tissue layer is covered by a fully differentiated epithelial layer as to also provide for wound cover.

Thus, in a first aspect, the present invention relates to a method for in vitro growing of connective tissue substitute, said connective tissue substitute being populated with fibroblasts, comprising the steps of: a) providing a connective tissue layer substantially free of living cells having a first and a second contacting side, the first contacting side being opposed to the second contacting side; b) placing the connective tissue layer in a container comprising fibroblasts, allowing the fibroblasts to contact the first contacting side of the connective tissue layer; and c) at least temporarily simultaneous with step b) contacting the second contacting side of the connective tissue layer, the connective tissue layer being positioned in the container, with a chemotactic factor providing environment, to attract said fibroblasts into the connective tissue layer by passing through the first contacting side of the said connective tissue layer. The connective tissue substitute according to the present invention is suitable for application onto a wound in a subject in need thereof.

In step a) a connective tissue layer substantially free of living cells, hereinafter also called "connective tissue layer", having a first and second contacting side, the first contacting side being opposed to the second contacting side, is provided. Said "connective tissue layer substantially free of living cells" (hereinafter also referred to as connective tissue layer) may be any connective tissue layer substantially free of living cells known in the art (see e.g. Molecular Biology of the Cell, 2nd edition, Chapter 14, ed. Alberts et al., Garland Publishing, Inc., New York, USA, incorporated herein by reference). As herein used, the term "connective tissue layer substantially free of living cells" is meant to comprise such a connective tissue layer derived from a donor organism that is treated as to remove or kill substantially all living cells (e.g. de-epidermised connective tissue, e.g. dermis (DED, or so-called second cut DED)) as well as artificial engineered connective tissue-type scaffolds, constructed from e.g. collagen, elastin, glycosaminoglycan, polyester and/or polycarbonate. As used in this context, substantially free of living cells is meant to indicate a cell survival rate of less than 5%, preferably less then 2%, more preferably of less than 1%, more preferably yet of less than 0.5% and most preferably of 0%.

Said connective tissue layer substantially free of living cells can for example be obtained by treatment of skin as to remove the epidermal layer and remove or kill substantially all the cells of the underlying dermal layer. The skilled person is aware of suitable methods to obtain such a connective tissue layer. As will be discussed below, the said connective tissue layer substantially free of living cells can preferably be obtained from a donor organism. Preferably, the structure of the connective tissue layer and the cell basement membrane are intact. Thus, a connective tissue layer substantially free of living cells is obtained, which is repopulated by fibroblasts, preferably fibroblasts of the subject that is to receive the connective tissue substitute. The connective tissue layer substantially free of living cells is shaped and sized to fit the wound of the subject that is to receive the connective tissue substitute as to provide for optimal wound closure.

In step b) the connective tissue layer is placed in a container comprising fibroblasts, allowing the fibroblast to contact the first contacting side of the connective tissue layer. The first contacting side is preferably faced down (implicating the second contacting side being faced up), and is more preferably in contact, yet more preferably in full contact, with the container via the fibroblasts contained therein, preferably with a bottom portion thereof, the bottom portion preferably being horizontally oriented.

The connective tissue layer substantially free of living cells has a first and a second contacting side. In the absence of a basement membrane attached to the connective tissue layer, the first or second contacting side can be chosen arbitrarily. However, when a basement membrane is present on one side of the connective tissue layer, the first contacting side that is to be contacted with the fibroblasts represents the side that does not have the basement membrane attached thereto, as fibroblasts substantially cannot penetrate the basement membrane in order to populate the connective tissue layer substantially free of living cells. Thus, in the presence of a basement membrane, the fibroblasts are to be contacted with the so-called reticular surface (the side of the connective tissue layer that does not have a basement membrane attached thereto) of the connective tissue layer. The side of the connective tissue layer that has a basement membrane attached to it (also called papillary surface), will therefore be the second contacting side that is to be contacted with the chemotactic factor providing environment.

The container may be any container known in the art, such as e.g. a cell culture dish, a Petri-dish, a well of a plate comprising wells, a flask, a transwell or the like. Said container may be made of plastic or of glass or of any other material suitable for containing cells. The container preferably comprises a flat bottom portion. The fibroblasts may form an adhering monolayer on the bottom portion of the container.

Said fibroblasts may be prepared by any method known in the art, such as for example culturing in a cell culture dish, flask or transwell.

In step c) the second contacting side of the connective tissue layer, the connective tissue layer being positioned in the container, is contacted at least temporarily simultaneous with step b) with a chemotactic factor providing environment, to attract said fibroblasts into the connective tissue layer by passing through the first contacting side of the said connective tissue layer. Preferably, the second contacting side is facing up, so that the chemotactic factor providing environment can conveniently be provided on top thereof.

As used herein, "chemotactic factor providing environment" is meant to indicate any environment that can accomplish migration of fibroblasts into the connective tissue layer. Non-limiting examples of such chemotactic factor providing environment are epithelial cells, epidermal cells, keratinocytes, cell extracts or culture supernatants of such cells, an intact epithelial layer, in particular an intact epidermal layer, or isolated factors known in the art for providing a chemical environment as to attract fibroblasts, such as chemokines, growth factors, cytokines, etc, or a mixture of one or more thereof.

The term "at least temporarily simultaneous" as used herein is meant to indicate that contacting of the fibroblasts in the container with the first contacting side of the connective tissue layer and contacting of the chemotactic factor providing environment with the second contacting side of the connective tissue layer takes place simultaneously at least temporarily, i.e. during a short period of time. It does not imply that either contacting step cannot take place without the other contacting step, as long as both contacting steps take place simultaneously during some period of time sufficiently to accomplish population of the connective tissue layer with the fibroblasts.

In this method, the connective tissue layer, e.g. DED, does not have to be turned over in order to obtain a fibroblast populated connective tissue substitute, as is the case in the method of Ghosh et al., supra, such that this method is more convenient than methods known to date. Moreover, primary isolates of fibroblasts, which do not have to be serially passaged, may advantageously be used, such that the time required for the preparation of such substitute can be reduced in comparison to the method disclosed in Dong-Youn Lee et al., supra. Thus, the method is more convenient and faster than known methods for obtaining fibroblast populated connective tissue substitute and allows for rapid preparation of fully autologous connective tissue substitute. For the preparation of a cell populated connective tissue only a single small biopsy is required from a subject in order for the substitute to be fully autologous. In addition, it has been shown the rate of wound healing is increased without any adverse scar tissue formation (no hypertrophic scar formation), when such connective tissue substitute is applied onto a wound, in particular when the fibroblast populated connective tissue substitute is covered with an epithelial layer. In addition to the connective tissue substitute according to the present invention, any convenient preparation for wound cover may be used as to prevent the wound from moisture loss and susceptibility to infection. One skilled in the art will be aware of suitable preparations as to provide wound cover, such as one or more of the commercial preparations as disclosed above.

The term "autologous" is well known in the art and refers to a subject's own tissue.

In a preferred embodiment, the container comprising fibroblasts is a cell culture dish or a transwell comprising fibroblasts. The cell culture container may be any cell culture container known in the art, such as a conventional cell culture dish, a well in a plate with wells or preferably a transwell. Preferably, according to the invention the fibroblasts are cultured in a cell culture container in fibroblast medium to about 50% confluence before being contacted with the connective tissue layer. In order to achieve migration of fibroblasts into the connective tissue layer and population of the connective tissue layer with the fibroblasts, the second contacting side of the connective tissue layer, i.e. the side of the connective tissue layer that is not contacted with the fibroblasts, is contacted with a chemotactic factor providing environment. Suitable media for culturing of fibroblasts are well known in the art and can therefore easily be determined by one skilled in the art. The fibroblasts in the cell culture container, such as cell culture dish or transwell, may be subjected to trypsinisation in order to accomplish release of the fibroblasts from the cell culture container, e.g. a cell culture dish or transwell. The latter is particularly relevant when an amplification of the fibroblasts is required. For construction of the fibroblast-populated connective tissue layer using a primary cell culture, trypsinisation is not required.

The second contacting side of the connective tissue layer is kept substantially free of contact with fibroblasts from the container. Thus, the connective tissue layer provides a barrier between the fibroblasts and the chemotactic factor providing environment. Due to the chemoattractant function of the chemotactic factor providing environment, fibroblasts tend to be attracted from the first contacting side of the connective tissue layer towards the second contacting side of the connective tissue layer, such that they populate the intermediate space.

In a preferred embodiment, the fibroblasts are a primary cell culture. This minimises the time required for the preparation of the connective tissue substitute, and yet provides sufficient fibroblasts as to populate the connective tissue layer. Thus, fibroblasts may be isolated from a subject, cultured for 3-6 days, and then contacted with the first contacting side of the connective tissue layer whilst also at least temporarily simultaneously contacting the second contacting side of the connective tissue layer with the chemotactic factor providing environment, e.g. an intact epithelial layer. Thus, the autologous connective tissue substitute can conveniently be prepared in about 2-3 weeks.

In one embodiment, said chemotactic factor providing environment is provided by a medium comprising one or more chemotactic factors. The one or more chemotactic factors represent the chemoattractant for the fibroblasts, such that these migrate into and populate the connective tissue layer. Said medium comprising one or more chemotactic factors may be any medium comprising chemotactic factors, such as e.g. a solution or other medium, such as a gel, oil, cream or a paste, comprising chemokines, growth factors, cytokines, etc, or a mixture of one or more thereof.

In a further embodiment, at least one chemotactic factor in the environment is derived from epithelial cells, such as e.g. a cell extract or cell culture supernatant of epithelial cells. Such cell extract or cell culture supernatant comprises a complex mixture of chemokines, cytokines, growth factors and other chemotactic factors, which are particularly suitable as chemotactic factor providing environment as to attract fibroblasts into the connective tissue layer.

In a preferred embodiment, said chemotactic factor providing environment comprises epithelial cells. Such epithelial cells secrete a complex mixture of chemokines, cytokines, growth factors and other chemotactic factors that attract fibroblasts into the connective tissue layer, such that the connective tissue layer gets populated with fibroblasts. Also, growth factor and cytokines secreted by fibroblasts stimulate epithelial proliferation, differentiation and migration over the connective tissue structures, such that the epithelial cells will form a well-differentiated epithelial layer which may provide wound cover in addition to wound closure.

In another embodiment, the epithelial cells comprise-keratinocytes, for the same reasons as disclosed above. Keratinocytes constitute the major component of epithelial cells, such that the same as above is true for keratinocytes.

It is preferred that the epithelial cells are epidermal cells. Most wounds are skin wounds, such that these are the major target of the method according to the present invention. Moreover, epidermal cells are relatively easy to acquire with minimum discomfort and stress for the subject.

In a more preferred embodiment, said chemotactic factor providing environment comprises an intact epithelial layer. This intact epithelial layer ensures the formation of a multi-layered well-differentiated epithelial layer on the second contacting side of the connective tissue layer, such that not only optimal wound closure, but also optimal wound cover is ensured by the thus obtained connective tissue substitute.

In case of growing a dermal tissue substitute for closing dermal wounds, epidermal layer is taken as epithelial layer. However, other epithelial tissue can be used according to the present invention, e.g. covering and mucosal epithelia of the oral cavities, stomach, intestine, ocular conjunctiva, urinary tract, and respiratory passage.

Said epithelial layer may be derived from any epithelial tissue, such as e.g. the tongue, oesophagus, the oral cavity, the cornea of the eye, respiratory tract or intestinal cavity, but is preferably an epidermal layer derived from skin tissue. For the preparation of skin tissue, the epidermal layer is used.

Said epithelial layer is grown onto the connective tissue layer substantially free of living cells. In case epithelial layer is used as chemotactic factor providing environment, an intact epithelial layer of the subject is placed onto the second contacting side of the connective tissue layer. According to the invention the said intact epithelial layer can be expanded at least about 20-fold in about 3 weeks, such that the surface area of the intact epithelial layer that is contacted with the second contacting side of the connective tissue layer may be ½₀th of the corresponding surface area of the connective tissue layer substantially free of living cells. The intact epithelial layer is preferably placed onto the second contacting side of the connective tissue layer in its physiological orientation. In case the epithelial layer is an epidermal layer, it is thus preferred that the side of the said epidermal layer naturally contacting the connective tissue layer via a basement membrane is contacted with the second contacting side of the connective tissue layer, whereas the side of the said epidermal layer naturally not contacting the connective tissue layer via the basement membrane is in contact with air as to stimulate proliferation and differentiation within the epidermal layer. Any method for obtaining an intact epithelial layer may be used; one skilled in the art will be aware of suitable methods to obtain an intact epithelial layer of a subject, e.g. enzymatic digestion of the skin with dispase or thermolysin, or incubation of skin in calcium or magnesium free solutions or EDTA containing solutions.

Preferably, according to the invention the epithelial layer will be contacted via the connective tissue layer with a keratinocyte growth medium for at least about 24 hours, allowing uptake and release of compounds necessary for growth. In this case, the layered assembly of connective tissue layer and epithelial layer is e.g. placed into keratinocyte culture medium with its connective tissue layer submerged in keratinocyte culture medium. Thus, the epithelial layer remains intact such that the tissue architecture is maintained, which facilitates expanding thereof. By growing the epithelial layer in this way, no time-consuming and costly amplification steps of cell suspensions are involved and very little biopsy material is required. In particular in the case of an epidermal layer, it is preferred that the epidermal layer is grown with the side opposing the side contacting the second contacting side of the connective tissue layer exposed to air as to stimulate complete differentiation of the epidermal layer. However, the epithelial layer may also be grown under submerged conditions. This may in some cases, for example in the case of growing epidermal tissue, result in partial rather than complete differentiation or may provide optimal culture conditions for other types of epithelial tissue, e.g. mucosal tissue.

The epithelial layer is preferably pre-grown onto the connective tissue layer substantially free of living cells in the presence of growth factor, such as a culture medium containing growth factor. One skilled in the art will readily be capable to establish and prepare a suitable culture medium containing growth factor. It is however preferred to use a culture medium comprising Dulbecco's modified Eagle's Medium/Hams F12 medium, serum or serum substitute and one or more growth factors. It is preferred that the serum is derived from the subject as thus risks associated with allogeneic material can be avoided. Alternatively, a serum substitute may be used for this purpose. Serum substitutes are well known in the art. Examples thereof are ultroserG, ultroserHY, bovine pituitary extract (all available from Life technologies), controlled process serum replacements (CPSR; available from Sigma) and bovine embryonic fluid (Sigma). As herein used, the term "growth factor" is meant to encompass all substances which stimulate optimal growth and differentiation of the epithelial layer, e.g. keratinocyte growth factor (KGF), epidermal growth factor (EGF), fibroblasts growth factors, transforming growth factor alpha, vascular endothelial growth factor, granulocyte monocyte colony stimulating factor, hormones such as testosterone and oestrogens, and cytokines such as interleukin-1α, interleukin-8 and growth related oncogene-α. It is preferred that the level of growth factor in the culture medium is in the range of 0.1-50, preferably 0.2-25, more preferably 0.5-15 and most preferably 1-10 ng/ml. Moreover, it is preferred that said culture medium further comprises vitamin C, which promotes proliferation and ceramide 6 synthesis, ceramide 6 being a component of the stratum corneum which is important for good barrier formation. Furthermore preferably said culture medium further comprises hydrocortisone and insulin, as best results are thus obtained. Optionally, said culture medium further comprises one or more antibiotics, such as penicillin, streptomycin, ampicillin, etc., or a combination thereof.

The epithelial layer is then allowed to grow on the second contacting side of the connective tissue layer to obtain a layered assembly of epithelial layer and connective tissue layer substantially free of living cells.

After at least 24 hours, the assembly of connective tissue layer substantially free of living cells and epithelial layer is removed from the keratinocyte culture medium and the first contacting side of the connective tissue layer substantially free of living cells is placed on top of a cell culture container, preferably a cell culture dish or transwell, wherein fibroblasts have been allowed to attach and cultured in fibroblast culture medium, as to attract the fibroblasts into the connective tissue layer substantially free of living cells. The thus obtained assembly of fibroblasts attached to a cell culture container in culture medium, connective tissue layer substantially free of living cells and epithelial layer is then contacted for a further 1-3 weeks. After 1-3 weeks of further incubation, the original outlines of the epidermal layer of the punch biopsies are still visible, whereas a fully differentiated epidermal layer has developed onto the connective tissue layer substantially free of living cells. The thus grown tissue substitute can be implanted into the subject, while the tissue is in fact preferably the subject's own tissue, thus providing no risk for graft rejection. When the tissue substitute is constructed from fibroblasts which have been isolated at an earlier time period than the intact epithelial layer (biopsies obtained at different times), the intact epithelial layer in contact with the second contacting side of the connective tissue layer does not have to first be cultured for at least 24 hours in keratinocyte culture medium. In this case the connective tissue layer substantially free of living cells and epithelial layer can be placed directly on the fibroblasts via the first contacting side of the connective tissue layer substantially free of living cells.

It was found that in such a simple manner in about 3 weeks the autologous epithelial layer could be expanded about 20-fold. In this time period, about 1.5 $cm^2$ of autologous epithelial layer could be obtained using a punch biopsy of epithelial layer with a diameter of about 3 mm. Most other skin models known in the art utilise single cell suspensions of keratinocytes to initiate growth of an epithelial layer. This is not only more time-consuming and costly, but it also requires a significantly greater amount of starting skin due to the high seeding density generally required to amplify keratinocytes before constructing the epithelial layer.

It is preferred that the intact epithelial layer is an intact epidermal layer, as skin wounds are the major target of the method according to the present invention, and an intact epidermal layer is easy to obtain with minimum discomfort and stress for the subject.

In a preferred embodiment of the method according to the present invention the epithelial cells, keratinocytes, or intact epithelial layer are obtained from the said subject, such that these provide for autologous tissue.

In a preferred embodiment of the method according to the present invention, the epithelial cells, keratinocytes, or intact epithelial layer are obtained from one or more skin biopsies of said subject. Any method for obtaining an intact epithelial layer may be used; one skilled in the art will be aware of suitable methods to obtain an intact epithelial layer, in particular an intact epidermal layer of a subject, e.g. enzymatic digestion of the skin with dispase or thermolysin, or incubation of skin in calcium or magnesium free solutions or EDTA containing solutions. The skilled person will also be aware of suitable methods for obtaining epithelial or epidermal cells, in particular keratinocytes from an intact epidermal layer, see e.g. Ghosh et al., supra.

In a preferred embodiment, the second contacting side of the connective tissue layer comprises a basement membrane. In case epithelial cells, keratinocytes or an intact epithelial layer are used as chemotactic factor providing environment in the preparation of the connective tissue substitute according to the present invention, this basement membrane is important as it allows for attachment of epithelial cells to the connective tissue layer.

As herein used, the term "basement membrane" is meant to include both natural and artificial basement membrane. In case the connective tissue layer substantially free of living cells is derived from a donor organism, it is preferred that the basement membrane naturally connected with the connective tissue layer substantially free of living cells is present. However, in case an artificial connective tissue-type scaffold is used or the natural basement membrane from the connective tissue layer substantially free of living cells derived from a donor organism is absent or damaged, an artificial basement membrane may be constructed, such as a layer of fibronectin, fibrin, collagen or any other substance, alone or in combination, permitting attachment of the epithelial layer to the connective tissue layer.

Moreover, it is preferred that the fibroblasts are obtained from one or more skin biopsies of said subject. As discussed above, skin biopsies are relatively easy to obtain with minimum discomfort for the subject. Moreover, it is relatively easy to isolate fibroblasts from such biopsies as to allow for further culturing of such fibroblasts, as will be discussed below.

The intact epithelial layer can be removed from the skin biopsy and the remaining skin tissue may be treated with dispase and collagenase to isolate at least the fibroblasts therefrom. Dispase and collagenase digest the structural connective tissue components such as e.g. collagen, and render several cell types, most importantly the fibroblasts, intact. Alternatively, the remaining skin tissue may be brought into culture intact and the fibroblasts may be allowed to migrate naturally out of the tissue at an albeit slower rate than obtained by enzymatic digestion of the remaining skin tissue. In addition to the fibroblasts several other cell types present within the connective tissue may be isolated and grown, such as e.g. endothelial cells. Thus, the cells are autologous to the subject being treated. It is preferred that the entire digest obtained is transferred to tissue culture as to obtain a connective tissue cellular mixture. This avoids the need to use time-consuming purification methods and results in better mimicking of the natural connective tissue cell composition.

Preferably, in the method according to the present invention the fibroblasts and the epithelial cells, keratinocytes, or intact epithelial layer are derived from the said subject, such that one singly biopsy is sufficient to provide both the fibroblasts and epithelial or epidermal cells or intact epithelial or epidermal layer. Thus, fully autologous connective tissue substitute can be obtained with minimal chance of graft rejection and minimal stress for the subject. The age of the subject is not a limiting factor for constructing the connective tissue substitute as it can be easily formed even from subjects above 90 years of age with biopsies obtained from all areas of the skin, including even extremely photoaged areas of the skin, such as e.g. skin from the neck or ear.

Preferably, the intact epithelial layer is removed from the biopsy and the remaining skin tissue is treated with dispase and collagenase to isolate at least fibroblasts therefrom. Dispase and collagenase digest the structural connective tissue components such as e.g. collagen, and render several cell types, most importantly the fibroblasts, intact. Alternatively, the remaining skin tissue may be brought into culture intact and the fibroblasts may be allowed to migrate naturally out of the tissue at an albeit slower rate than obtained by enzymatic digestion of the remaining skin tissue. The fibroblasts are grown to repopulate the connective tissue layer substantially free of living cells as to mimic the situation in a natural connective tissue layer. In addition to the fibroblasts several other cell types present within the connective tissue may be isolated and grown, such as e.g. endothelial cells. Thus, the cells are autologous to the subject being treated. It is preferred that the entire digest obtained is transferred to tissue culture as to obtain a connective tissue cell mixture. This avoids the need to use time-consuming purification methods and results in better mimicking of the natural connective tissue cell composition.

In a further embodiment, the method according to the present invention further comprises the step of introducing one or more nucleotide sequences into the fibroblasts, epithelial cells, keratinocytes or intact epithelial layer to provide for gene therapy. The said one or more nucleotide sequences may be DNA sequences, RNA sequences or any combination thereof. Said nucleotide sequences may be prepared by any method known in the art, such as recombinant DNA technology or in vitro synthesis. Said nucleotide sequence may be introduced by any method known in the art, such as transient transfection or transformation, and may either be incorporated into the chromosome of cells of the epithelial layer and/or fibroblasts or may be maintained into said cells and/or fibroblasts as autonomously replicating nucleotide sequences, such as autonomously replicating vectors. Said nucleotide sequences are preferably operably linked to control sequences such as promoters and terminators. Said nucleotide sequences may for example encode proteins of interest for e.g. treatment of certain diseases. Insulin expressing nucleotide sequences may for example be introduced for treatment of diabetes. Similarly, basement membrane zone proteins (e.g.: collagen VII) expressing nucleotide sequences may for example be introduced for treatment of bullous (blistering) diseases, or granulocyte macrophage colony stimulating factor (GM-CSF) may be introduced to aid cancer therapies. Alternatively, said nucleotide sequences may provide for an antisense sequence, e.g. to target and inactivate specific mRNAs. In this way, anti-sense tumor necrosis factor alpha (TNF-α) may be introduced for counteracting the overexpression of TNF-α in inflammatory disorders such as psoriasis and arthritis.

It is preferred that said connective tissue layer substantially free of living cells is derived from a donor organism, said subject not being said donor organism. Preferably, such said connective tissue layer substantially free of living cells is derived from skin of a donor organism. Such skin generally comprises an epidermal layer, basement membrane and dermal layer. According to the invention, said skin is treated to remove the epidermal layer whilst rendering the structure of the dermal layer and preferably the basement membrane intact. Preferably, the dermal cells are substantially removed from the dermal layer. A skilled practitioner will be aware of suitable methods for treatment of skin for the present purposes. A method that may be used for such a purpose can e.g. be treatment of the skin with calcium and magnesium free saline, followed by careful scraping off of the epidermal layer, or enzymatic removal of the epidermal layer with e.g. dispase and/or thermolysin. Skin can be obtained from slaughtered or dead organisms, in which case such skin is referred to as cadaver skin.

It is highly preferred that such skin is human skin, as to produce the epithelial layer from entirely human components and avoid the use of non-human material as to exclude risks associated therewith, such as e.g. the risk of Kreutzfeld-Jacobs disease. Examples of such human skin are e.g. foreskin or skin of passed-away donors.

In a second aspect, the present invention relates to a connective tissue substitute obtainable by the method according to the present invention, and in particular to a dermal tissue substitute, more in particular a skin substitute, obtainable by the method according to the present invention.

The connective tissue substitute, and in particular the dermal tissue substitute, is populated with at least fibroblasts and may also contain other cells. Preferably, all cells in the product are autologous to the subject being treated, whereas the non-cellular structure of the connective tissue layer still originates from an allogeneic connective tissue layer donor, preferably of human origin.

In the case of a dermal tissue substitute, it may comprise additional dermal cells such as e.g. endothelial cells. The dermal tissue substitute may or may not comprise an epidermal layer. In case the dermal tissue substitute comprises an epidermal layer, it may also be called skin substitute or skin tissue substitute. Preferably, it will comprise such an epithelial layer, which is fully differentiated and closely resembles the native epidermis (in case intact epithelial layer is used for the preparation of the connective tissue substitute, its final structure will closely resemble native epidermis). The epithelial layer preferably consists of a basal layer, spinous layer, granular layer and stratum corneum. The stratum corneum is important for the barrier function of the epidermis reducing the risk of infection and excessive water loss. This is of major importance for subjects with chronic and/or large wounds. Proliferating keratinocytes are only found in the basal layer at a similar frequency to that found in native healthy epidermis. Keratins important for keratinocyte migration during wound closure, such as e.g. keratins 6 and 16, are up-regulated to a similar extent to that found in epidermis during wound closure. Expression of proteins required for cornified envelope formation and normal epidermal differentiation, such as loricrin, involucrin, small proline rich protein 2 (SPRR2) and keratin 10, are up-regulated only in the expanding flanks of the skin tissue substitute similar to epidermis during wound closure. The potential anti-inflammatory regulatory proteins, e.g. skin derived antileukoproteinase, are up-regulated in the skin tissue substitute. Moreover, the skin tissue substitute secretes a number of chemokines and angiogenic factors likely to stimulate angiogenesis, such as CCL2/MCP-1, CXCL8/IL-8, CCL27/CTACK, vascular endothelial growth factor (VEGF), fibroblast growth factors (e.g. FGFs) and hepatocyte growth factor (HGF).

It is possible to incorporate pigment forming cells, melanocytes, into the epidermis such that normal pigmentation of the graft will be obtained. This would make use of the dermal tissue substitute for treatment of pigment disorders such as vitiligo possible.

Preferably, fibroblasts populate the entire dermis at a similar frequency to that found in native healthy dermis. These fibroblasts are not differentiated into myofibroblasts, thus reducing the risk of hypertrophic scar formation. It is possible to incorporate endothelial cell into the dermis, which may further facilitate angiogenesis and decrease the chance of graft rejection.

Thus, the autologous dermal tissue substitute preferably resembles full-thickness skin in that it consists of an epidermal component and a dermal component, which makes it a relatively strong graft. Grafts consisting only of an acellular dermal component, such as e.g. Alloderm®, are open to infection and water loss, and furthermore epidermis has to be generated from the wound edges. In contrast therewith, grafts consisting of only an epidermal component are generally very fragile. The basement membrane has to be formed with the dermis present in the wound bed, which is a process that takes a number of weeks to months. Furthermore, these grafts are not as fully differentiated as full skin grafts composed of epidermal layer, basement membrane and cellular dermal layer. Therefore, the barrier aspect of such a graft comprising only of an epidermal layer will be inferior to the full skin graft.

It is also envisaged that the connective tissue substitute, in particular a dermal tissue substitute, may be used for studies that are conventionally conducted on animal or human skin. Examples of such studies are toxicology studies for mammals, in particular humans, and immunological studies such as studies for allergenic reactions. Moreover, the tissue substitute may be used for testing of cosmetic products as to reduce, avoid or eliminate the use of testing animals for such purposes.

In a further aspect, the present invention relates to a method for closing of a wound, comprising the step of applying a connective tissue substitute onto a wound. The connective tissue substitute may be prepared to fit the wound and may be applied to provide wound closure. As such, it was found that the connective tissue substitute, in particular a dermal tissue substitute, will migrate onto the edges of the wound and eventually immerse with the subject's skin. The wound will thus fully heal. Importantly, the dermal tissue substitute was indistinguishable from the subject's skin.

The wound may be any wound, but is preferably a chronic wound or an acute wound. Preferably, the chronic wound is chosen from the group, consisting of a venous ulcer, arterial ulcer, diabetic ulcer, decubitus and persisting burn wound. Preferably, the acute wound is chosen from the group, consisting of a surgical wound, accidental wound, decubitus and burn wound. It was found that such wounds were easily closed using the connective tissue substitute, in particular a dermal tissue substitute, according to the present invention.

Further, the present invention relates to a method for treating a subject suffering from a wound, comprising applying the connective tissue substitute according to the present invention onto said wound. Thus, a patient in need thereof can be treated with the cell populated connective tissue substitute as to stimulate the wound bed and thus stimulate repair. It is preferred that the connective tissue substitute is a full-thickness dermal tissue substitute comprising a dermal and an epidermal layer. Growing of the connective tissue substitute according to the present invention may take between two and three weeks.

EXAMPLES AND FIGURE

Hereinafter, the present invention is further illustrated by means of the following examples which are shown merely to illustrate embodiments of the present invention, and not to limit it in any way, and FIG. 1, which depicts an embodiment of a method for the preparation of a dermal tissue substitute according to the present invention.

Referring to the left part of FIG. 1, reference number 4 denotes a cadaver skin comprising an epidermal layer 5 and a connective tissue layer 6 having a basement membrane 7 located in between. At this stage, the cadaver skin 4 comprises numerous cells. From the cadaver skin 4, the cells are removed e.g. by treatment with calcium and magnesium free phosphate buffered saline containing penicillin and streptomycin as e.g. indicated in example 1 below resulting in a connective tissue layer 1 substantially free of living cells (arrow. I). The connective tissue layer 1 substantially free of living cells has a first contacting side 2 and a second contacting side 3 that are opposed to each other. The second contacting side 3 preferably comprises the basement membrane 7, which can e.g. be achieved by gently scraping the epidermal layer 5 off the connective tissue layer 1 substantially free of living cells. This connective tissue layer 1 substantially free of living cells, optionally having a basement membrane 7 attached to the second contacting side 3 thereof, may be stored up until use, e.g. as indicated in example 1 below.

Now referring to the right part of FIG. 1, a full-thickness skin punch biopsy 8 is shown which may be of human origin. The punch biopsy 8 comprises an epidermal layer 9 and a dermal layer 10 which are separated through a basement membrane 11. The epidermal layer 9 comprises epithelial cells 12. The dermal layer 10 comprises fibroblasts 13. From the punch biopsy 8, the epidermal layer 9 and the dermal layer 10 are separated from one another (arrow II), e.g. by dispase treatment, e.g. as described in example 2 below. The intact epidermal layer 9 is carefully removed (see left splitting side of arrow II). The dermal layer 10 comprising basement membrane 11 attached thereto remains intact (see right splitting side of arrow II).

The connective tissue layer 1 substantially free of living cells is placed in a container 14 (arrow III), which may be any cell culture container but is in this case a transwell. The intact epidermal layer 9 is placed onto the connective tissue layer 1 substantially free of living cells (arrow IV) to obtain a layered assembly 15 of epidermal layer 9 and connective tissue layer 1 substantially free of living cells. In case the connective tissue layer 1 substantially free of living cells 1 comprises a basement membrane 7, the epidermal layer 9 is placed onto the basement membrane 7 attached to the second contacting side 3, such that the connective tissue layer 1 substantially free of living cells and the epidermal layer 9 are separated by the basement membrane 7. Culture medium 16 is added until it contacts the epidermal layer 9 from underneath, with the stratum corneum side 17 of the epidermal layer 9 upwards. The above is e.g. disclosed in example 3.

Now referring to the right splitting side of arrow II, after removal of the epidermal layer 9 from the punch biopsy 8, the fibroblasts 13 are isolated from the dermal layer 10 e.g. by treatment with dispase/collagenase. The fibroblasts 13 are cultured in a second container 17 (see arrow V) e.g. as described in example 4 below.

After growing of the fibroblasts 13 for several days, in which case it concerns a primary cell culture, the layered assembly 15 is placed with the epidermal layer 9 upwards contacting air onto the fibroblasts 13 grown in the second container 17 (arrows VI and VII), as e.g. described in example 5 below. The epidermal layer 9 constitutes the chemotactic factor providing environment to attract the fibroblasts 13 into the connective tissue layer 1 substantially free of living cells by passing through the first contacting side 2 of the connective tissue layer 1 substantially free of living cells. The resultant was allowed to grow for a further several days to allow population of the connective tissue layer 1 substantially free of living cells with fibroblasts 13 to obtain a fibroblast-populated dermal tissue substitute 18 (arrow VIII).

Example 1

Preparation of a Connective Tissue Layer Substantially Free of Living Cells Glycerol preserved human cadaver skin from the Euro Skin Bank (Beverwijk, The Netherlands) was washed in calcium and magnesium free phosphate buffered saline (PBS). The cadaver skin was incubated for 1 week at 37° C. in calcium and magnesium free PBS containing penicillin (100 IU/ml) and streptomycin (100 µg/ml) with three renewals of the calcium and magnesium free PBS containing penicillin and streptomycin during this week. The epidermis could be gently scraped off using a blunt metal spatula leaving the dermal layer substantially free of living cells and the basement membrane that was attached to the papillary surface thereof intact. The dermal layer comprising a basement membrane was stored in calcium and magnesium free PBS containing penicillin and streptomycin for up to 6 months at 4° C. until it was used.

Example 2

Preparation of an Intact Epidermal Layer 3 mm full-thickness skin punch biopsies were removed from a subject under sterile conditions from healthy areas of the skin which were not photoaged, such as e.g. the upper leg. In order to do so, the skin area was first cleaned using a chlorhexidine solution (1% in water) and allowed to dry. For each square centimetre of wound to be closed, a 3 mm biopsy was obtained.

Biopsies were washed in PBS and placed epidermal side upwards on a gauze swab soaked with dispase (Grade II; Boehringer). The biopsies were incubated overnight at 4° C. A biopsy was placed in a 9 cm culture dish containing PBS. The intact epidermal layer was carefully removed with sterile tweezers. Due to the hydrophobic lipid component in the stratum corneum, the epidermal layer floats with the stratum corneum side upwards thus enabling the orientation of the epidermal layer to be determined and also easily spooned up with a sterile flat spoon.

Example 3

Preparation of an Assembly of Epidermal Layer and Dermal Layer

The dermal layer obtained in example 1 was cut to fit the wound onto which it was to be applied (1 cm×2 cm) and incubated overnight in culture medium I (Dulbecco's modification of Eagle's medium (DMEM)/Hams F12 (3:1), 1% ultroserG (Biosepra S.A., Cergy-Saint-Christophe, France), $10^{-7}$ M insulin, $10^{-6}$ M hydrocortisone, $10^{-6}$ M isopreteronol, 100 IU/ml penicillin, 100 µg/ml streptomycin containing 4 ng/ml KGF and 1 ng/ml EGF).

The dermal layer was placed with its basement membrane side upwards onto a sterile stainless steel grid. Culture medium I was added until the medium reached the bottom side of the dermal layer, with the top side of the dermal layer (the papillary surface or the so-called second contacting side) comprising a basement membrane being exposed to air.

On day 1, the intact epidermal layer obtained in example 2 was placed on top of the basement membrane (second contacting side) with its stratum corneum side upwards to form a layered assembly of epidermal layer, basement membrane and dermal layer. The epidermal layer on top of the dermal layer was cultured exposed to air with culture medium I contacting the epidermal layer from underneath until day 4. Then, the epidermal layer was contacted from underneath with culture medium II (DMEM/Hams F12 (3:1), 0.2% ultroserG (Biosepra S.A., Cergy-Saint-Christophe, France), $10^{-7}$ M insulin, $10^{-6}$ M hydrocortisone, $10^{-6}$ M isopreteronol, 0.1 M serine, $10^{-6}$ M carnitine, a lipid mixture containing essential fatty acids (final concentrations: 25 µM palmitic acid, 15 µM linoleic acid and 7 µM arachidonic acid using 24 µM essentially fatty acid free bovine serum albumin as a carrier protein), 130 µg/ml vitamin C phosphate, 1 µM vitamin E (DL-α-tocopherol-Ac), 100 IU/ml penicillin, 100 µg/ml streptomycin) containing 4 ng/ml KGF and 1 ng/ml EGF for a further 3-5 days with 1 optional renewal of the culture medium at day 7 (after 3 days).

On day 7-9, the epidermal layer had expanded approximately 1-2 mm from the edges of the original epidermal sheet over the dermal layer.

Example 4

Preparation of Fibroblast Culture Using Fibroblasts of the Subject

After removal of the epidermal layer from the biopsies, the remaining dermis was incubated for 2 hours at 37° C. in 0.5 ml dispase/collagenase in Hank's buffered salt solution (2.5 ml dispase type II, 75 mg collagenase and 7.5 ml Hank's solution; filter sterilised). Then 2 ml fibroblast medium (DMEM containing 1% ultroserG (Biosepra S.A., Cergy-Saint-Christophe, France), 100 IU/ml penicillin and 100 µg/ml streptomycin) was added and the digested dermis was centrifuged for 6 min at 1100 rpm. The pellet was resuspended in 2 ml fibroblast medium and transferred to a tissue culture 0.4 µm pore size transwell (Costar). Fibroblasts were cultured in a cell culture transwell in fibroblast medium for 7-9 days until 40-60% confluence. Medium was renewed at day 4 and optionally at day 7.

Example 5

Culturing of Dermal Tissue Substitute onto Fibroblasts

The layered assembly of epidermal layer, basement membrane and dermal layer substantially free of living cells was placed with the epidermal layer upwards contacting the air onto the fibroblasts cultured in the cell culture transwell and the resultant was allowed to grow for a further 7-14 days in culture medium II. KGF and EGF were maintained in culture medium II until the epidermis had expanded 3-5 mm from the edges of the epidermal sheet over the dermal layer and then were omitted. Therefore, after a total culture period of 2-3 weeks the growing epidermis completely covered the dermal layer having a basement membrane attached thereto on the second contacting side, and fibroblasts migrated into the dermis to obtain a dermal tissue substitute. During this growth period, culture medium II was renewed twice a week. Penicillin and streptomycin were omitted from the last medium renewal to avoid possible adverse drug reactions.

Example 6

Treatment of a Subject Using Dermal Tissue Substitute

Subject 1

A 71 year old male subject had a venous stasis leg ulcer for more than 6 months. The ulcer was approximately 1 cm×2 cm and the surrounding skin was inflamed.

2×3 mm skin punch biopsies were taken from the subject's upper leg, and the method disclosed in examples 1-5 was used to prepare autologous dermal tissue substitute. The dermal tissue substitute was ready for transplantation three weeks after taking the biopsies. It was placed on top of the ulcer and held in place with the aid of sterile gauze and bandage. The patient was advised to move the leg as little as possible during the first 5 days.

Within one day after applying the transplant the level of pain experienced by the patient decreased significantly.

Eight days after transplantation the autologous dermal tissue substitute was clearly visible on the wound bed and the epidermis of the skin tissue substitute was migrating out onto the subject's surrounding skin. Noticeable was that inflammation of the surrounding skin was less than before transplantation.

Three weeks after transplantation inflammation was decreased over the entire ulcer area. The dermal tissue substitute had turned slightly red indicating that it was developing a blood supply and angiogenesis was occurring.

Five weeks after transplantation only a small area of the dermal tissue substitute could still be distinguished from the surrounding tissue. This area of the dermal tissue substitute was slightly red indicating that it had a good blood supply. The rest of the dermal tissue substitute was now indistinguishable from the subject's skin. The area where the ulcer had previously been was no longer inflamed.

Seven weeks after transplantation the ulcer was completely healed and the dermal tissue substitute was nearly indistinguishable from the surrounding tissue. Thus, the cosmetic result was excellent.

Subject 2

A 73 year old female subject had 2 venous stasis leg ulcers for more than 6 months. The ulcers were both approximately 2 cm$^2$ each and the surrounding skin was inflamed.

5×3 mm skin punch biopsies were taken from the subject's upper leg, and the method disclosed in examples 1-5 was used to prepare 2 autologous dermal tissue substitutes. Three weeks after taking the biopsies, the dermal tissue substitutes were ready for transplantation. They were each placed on one of the ulcers and held in place with the aid of sterile gauze and bandage. The patient was advised to move the leg as little as possible during the first 5 days.

Similarly as with subject 1, within one day after applying the dermal tissue substitute the patient experienced significantly less pain.

Five days after transplantation, the autologous dermal tissue substitutes were clearly visible on the wound bed.

Two weeks after transplantation, only a small area of the dermal tissue substitutes could still be distinguished from the surrounding tissue. This area of the dermal tissue substitutes was slightly red indicating that it had a good blood supply. The rest of the dermal tissue substitute was now indistinguishable from the subject's skin.

Three weeks after transplantation the ulcers were fully healed and the dermal tissue substitutes were indistinguishable from the surrounding tissue. The area where the ulcer had previously been was no longer inflamed. Thus, the cosmetic result was excellent.

Subject 3

A 50 year old male subject had a decubitus wound on the heel for 10 months. The wound was approximately 3 cm$^2$.

2×3 mm skin punch biopsies were taken from the subject's upper leg, and the method disclosed in examples 1-5 was used to prepare an autologous dermal tissue substitutes. Three weeks after taking the biopsies, the dermal tissue substitute was ready for transplantation. It was placed on the wound and held in place with the aid of sterile gauze and bandage. The patient was advised to move the foot as little as possible during the first 5 days.

Similarly as with subject 1, within one day after applying the dermal tissue substitute the patient experienced significantly less pain.

Five days after transplantation, the autologous dermal tissue substitute was clearly visible on the wound bed.

Ten days after transplantation, only a small area of the dermal tissue substitute could still be distinguished from the surrounding tissue. This area of the dermal tissue substitutes was slightly red indicating that it had a good blood supply. The rest of the dermal tissue substitute was now indistinguishable from the subject's skin. 16 days after transplantation the wound was fully healed and the dermal tissue substitute was indistinguishable from the surrounding tissue. Thus, the cosmetic result was excellent.

Subject 4

A 78 year old female subject had 1 venous stasis leg ulcer for more than 14 years. The ulcer was approximately 130 cm$^2$.

A 6 cm$^2$ oval shaped biopsy was taken from the subject's abdominal area and subsequently biopsied into 40×3 mm biopsies in the tissue culture laboratory. Hereafter, the method disclosed in examples 1-5 was used to prepare autologous dermal tissue substitutes each of approximately 4 cm$^2$. Three weeks after taking the biopsy, the dermal tissue substitutes were ready for transplantation. They were each placed on the ulcer and held in place with the aid of sterile gauze and bandage. The patient was advised to move the leg as little as possible during the first 5 days.

Similarly as with subject 1, within one day after applying the dermal tissue substitute the patient experienced significantly less pain.

Five days after transplantation, the autologous dermal tissue substitutes were clearly visible on the wound bed.

Two weeks after transplantation, approximately 50% of the dermal tissue substitutes were attached and could still be distinguished from the surrounding tissue. This area of the dermal tissue substitutes was slightly red indicating that it had a good blood supply. The rest of the dermal tissue substitutes had now come loose and were discarded. However, during this time, wound healing had been stimulated to such a degree that the ulcer was clearly healing.

Eight weeks after transplantation the ulcer was almost closed (only 8 cm$^2$ was still open and still healing) and the dermal tissue substitutes were indistinguishable from the surrounding tissue.

The invention claimed is:

1. A method for in vitro growing of connective tissue substitute, said connective tissue substitute being populated with fibroblasts, said connective tissue substitute being suitable for application onto a wound in a subject in need thereof, said method comprising the steps of:
    a) providing a connective tissue layer substantially free of living cells having a first and a second contacting side, the first contacting side being opposed to the second contacting side;
    b) placing the connective tissue layer in a container comprising fibroblasts, allowing the fibroblasts to contact the first contacting side of the connective tissue layer; and
    c) at least temporarily simultaneous with step b) contacting the second contacting side of the connective tissue layer, the connective tissue layer being positioned in the container, with an intact epithelial layer, to attract said fibroblasts into the connective tissue layer by passing through the first contacting side of the said connective tissue layer.

2. A method according to claim 1, wherein the container comprising fibroblasts is a cell culture dish or a transwell comprising fibroblasts.

3. A method according to claim 1, wherein the second contacting side of the connective tissue layer is kept substantially free from contact with fibroblasts from the container.

4. A method according to claim 1, wherein the fibroblasts are a primary cell culture.

5. A method according to claim 1, wherein the intact epithelial layer is an intact epidermal layer.

6. A method according to claim 1, wherein the intact epithelial layer is derived from the said subject.

7. A method according to claim 1, wherein the epithelial layer is derived from the tongue, oesophagus, the oral cavity, the cornea of the eye, respiratory tract or intestinal cavity.

8. A method according to claim 1, wherein the intact epithelial layer is obtained from one or more skin biopsies of said subject.

9. A method according to claim 1, wherein the intact epithelial layer is obtained from one or more oral biopsies of said subject.

10. A method according to claim 1, wherein the second contacting side of the connective tissue layer comprises a basement membrane.

11. A method according to claim 1, wherein the fibroblasts are obtained from one or more skin biopsies of said subject.

12. A method according to claim 1, wherein the fibroblasts are obtained from one or more oral biopsies of said subject.

13. A method according to claim 1, wherein the fibroblasts and intact epithelial layer are derived from the said subject.

14. A method according to claim 1, further comprising the step of introducing one or more nucleotide sequences into the fibroblasts and/or intact epithelial layer.

15. A method according to claim 1, said connective tissue layer substantially free of living cells being derived from a donor organism, said subject not being said donor organism.

16. A method for in vitro growth of connective tissue substitute, said connective tissue substitute being populated with fibroblasts, said connective tissue substitute being suitable for application onto a wound in a subject in need thereof, said method comprising the steps of:
   a) providing a connective tissue layer substantially free of living cells having a first and a second contacting side, the first contacting side being opposed to the second contacting side;
   b) placing the connective tissue layer in a container comprising fibroblasts, allowing the fibroblasts to contact the first contacting side of the connective tissue layer; and
   c) contacting the second contacting side of the connective tissue layer with an epithelial layer for a short period of time during which the fibroblasts are simultaneously in contact with the first contacting side, the connective tissue layer being positioned in the container, to attract said fibroblasts into the connective tissue layer by passing through the first contacting side of the said connective tissue layer.

17. The method of claim 16, wherein the short period of time is 24 hours.

18. A method for in vitro growth of connective tissue substitute, said connective tissue substitute being populated with fibroblasts, said connective tissue substitute being suitable for application onto a wound in a subject in need thereof, said method comprising the steps of:
   a) providing a connective tissue layer substantially free of living cells having a first and a second contacting side, the first contacting side being opposed to the second contacting side;
   b) placing the connective tissue layer in a container comprising fibroblasts, allowing the fibroblasts to contact the first contacting side of the connective tissue layer; and
   c) contacting the second contacting side of the connective tissue layer with a chemotactic factor providing environment for a short period of time during which the fibroblasts are simultaneously in contact with the first contacting side, the connective tissue layer being positioned in the container, to attract said fibroblasts into the connective tissue layer by passing through the first contacting side of the said connective tissue layer.

* * * * *